(12) United States Patent
Fukumoto et al.

(10) Patent No.: US 10,005,808 B2
(45) Date of Patent: Jun. 26, 2018

(54) CRYSTAL OF ALKALI METAL N-ACETYLNEURAMINATE ANHYDRATE, AND PROCESS FOR PRODUCING SAME

(71) Applicant: KYOWA HAKKO BIO CO., LTD., Tokyo (JP)

(72) Inventors: Kazunari Fukumoto, Tokyo (JP); Masahiro Abe, Tokyo (JP)

(73) Assignee: KYOWA HAKKO BIO CO., LTD., Tokyo (JP)

( * ) Notice: Subject to any disclaimer, the term of this patent is extended or adjusted under 35 U.S.C. 154(b) by 0 days. days.

(21) Appl. No.: 15/500,020

(22) PCT Filed: Jul. 29, 2015

(86) PCT No.: PCT/JP2015/071475
§ 371 (c)(1),
(2) Date: Jan. 27, 2017

(87) PCT Pub. No.: WO2016/017677
PCT Pub. Date: Feb. 4, 2016

(65) Prior Publication Data
US 2017/0253627 A1    Sep. 7, 2017

(30) Foreign Application Priority Data
Jul. 30, 2014   (JP) ................................ 2014-154969

(51) Int. Cl.
*C07H 7/02*   (2006.01)
(52) U.S. Cl.
CPC ............ *C07H 7/02* (2013.01); *C07B 2200/13* (2013.01)
(58) Field of Classification Search
None
See application file for complete search history.

(56) References Cited

U.S. PATENT DOCUMENTS

| 4,698,332 A | 10/1987 | Ogasawara et al. |
| 5,231,177 A | 7/1993 | Saito et al. |

FOREIGN PATENT DOCUMENTS

| JP | 63-28411 B2 | 6/1988 |
| JP | H02-235897 A | 9/1990 |
| JP | 2745059 B2 | 4/1998 |

OTHER PUBLICATIONS

Flippen, "The Crystal Structure of β-D-N-Acetylneuraminic Acid Dihydrate (Sialic Acid), $C_{11}H_{19}NO_9 \cdot 2H_2O$", *Acta Crystallographica Section B*, B29: 1881-1886 (1973).
Ogura et al., "Stereochemical Characterization of Hydrated and Dehydrated Crystals of N-Acetylneuraminic Acid as Revealed by the IR, CD, and $^{13}C$ Cross Polarization-Magic Angle Spinning NMR Spectroscopy," *Chemistry Letters*, 6: 1003-1006 (1984).
Japanese Patent Office, International Search Report in International Patent Application No. PCT/JP2015/071475 (dated Oct. 6, 2015).

*Primary Examiner* — Layla D Berry
(74) *Attorney, Agent, or Firm* — Leydig, Voit & Mayer, Ltd.

(57) ABSTRACT

According to the present invention, a crystal of an alkali metal N-acetylneuraminate anhydrate, and a process for producing a crystal of an alkali metal N-acetylneuraminate anhydrate, comprising adding or adding dropwise a solvent selected from the group consisting of alcohols and ketones to an aqueous N-acetylneuraminic acid solution containing an alkali metal-containing compound and having a pH of 3.0 to 9.0 to precipitate a crystal of an alkali metal N-acetylneuraminate anhydrate, and collecting the crystal of an alkali metal N-acetylneuraminate anhydrate from the aqueous solution, can be provided.

14 Claims, 5 Drawing Sheets

CRYSTAL OF ALKALI METAL N-ACETYLNEURAMINATE ANHYDRATE, AND PROCESS FOR PRODUCING SAME

CROSS-REFERENCE TO RELATED APPLICATIONS

This patent application is the U.S. national phase of International Patent Application No. PCT/JP2015/071475, filed on Jul. 29, 2015, which claims the benefit of Japanese Patent Application No. 2014-154969, filed on Jul. 30, 2014, the disclosures of which are incorporated herein by reference in their entireties for all purposes.

TECHNICAL FIELD

The present invention relates to a crystal of an alkali metal N-acetylneuraminate anhydrate, which is useful, for example, as a product, a raw material, an intermediate or the like of health food, pharmaceuticals, cosmetics, and the like, and a production process thereof.

BACKGROUND ART

N-Acetylneuraminic acid (hereinafter, referred to as NeuAc) is a kind of acidic amino sugar generically called sialic acid and is widely used as a raw material of pharmaceuticals such as an anti-influenza drug, or as a component of food, cosmetics and bacterial media.

NeuAc can be produced by a fermentation method, an enzyme method, an extraction method from natural products, a chemical synthesis method, or the like. As the known NeuAc crystal, crystals of a dihydrate (Non-Patent Document 1) and an anhydrate (Non-Patent Document 2) are known, but a solution of these crystals shows strong acidity, and the degree of solubility thereof is relatively low of about 100 g/L at normal temperature. Furthermore, there is a problem with storage stability, for example, the crystal and a solution thereof are gradually discolored to dark brown.

On the other hand, as to the crystal of a neutralized salt of NeuAc, a crystal of NeuAc sodium salt trihydrate is known (Patent Document 1). This crystal exhibits high storage stability at normal temperature but has a problem with stability in high temperature conditions because of its low melting point near 100° C.

Under these circumstances, a crystal of a neutralized salt of NeuAc, having high storage stability at normal temperature as well as in high temperature conditions, is demanded.

RELATED ART

Patent Document

Patent Document 1: Publication of Japanese Patent Application No. H1-55388

Non-Patent Document

Non-Patent Document 1: Acta Crystallographica Section B: Structural Crystallography and Crystal Chemistry (1973), 29, pp. 1881-1886
Non-Patent Document 2: Chemistry Letters (1984), 6, pp. 1003-1006

SUMMARY OF THE INVENTION

Problems that the Invention is to Solve

An object of the present invention is to provide a crystal of a neutralized salt of NeuAc, having high storage stability at normal temperature as well as in high temperature conditions, and provide a production process thereof.

Means for Solving the Problems

The present invention relates to following (1) to (13).

(1) A crystal of NeuAc alkali metal salt anhydrate.
(2) The crystal described in (1) above, wherein the alkali metal salt is a sodium salt or a potassium salt.
(3) The crystal described in (1) above, wherein the alkali metal salt is a sodium salt.
(4) The crystal described in (1) above, wherein the alkali metal salt is a potassium salt.
(5) The crystal described in (3) above, wherein the crystal has peaks at diffraction angles (2θ) of 11.30±0.20°, preferably ±0.10°, 14.60±0.20°, prefereably ±0.10°, 19.80±0.20°, preferably ±0.10°, 21.70±0.20°, preferably ±0.10°, and 22.02±0.20°, preferably ±0.10° in powder X-ray diffraction.
(6) The crystal described in (5) above, wherein the crystal further has peaks at diffraction angles (2θ) of 11.12±0.20°, preferably ±0.10°, 19.16±0.20°, preferably ±0.10°, 24.62±0.20°, preferably ±0.10°, 25.70±0.20°, preferably ±0.10°, and 37.04±0.20°, preferably ±0.10° in powder X-ray diffraction.
(7) The crystal described in (6) above, wherein the crystal further has peaks at diffraction angles (2θ) of 19.46±0.20°, preferably ±0.10°, 24.14±0.20°, preferably ±0.10°, 25.56±0.20°, preferably ±0.10°, 31.34±0.20°, preferably ±0.10°, and 35.86±0.20, preferably ±0.10° in powder X-ray diffraction.
(8) The crystal described in (4) above, wherein the crystal has peaks at diffraction angles (2θ) of 10.76±0.20°, preferably ±0.10°, 14.76±0.20°, preferably ±0.10°, 21.24±0.20°, preferably ±0.10°, 22.92±0.20°, preferably ±0.10°, and 25.64±0.20°, preferably ±0.10° in the powder X-ray diffraction.
(9) The crystal described in (8) above, wherein the crystal further has peaks at diffraction angles (2θ) of 17.86±0.20°, preferably ±0.10°, 20.18±0.20°, preferably ±0.10°, 23.20±0.20°, preferably ±0.10°, 23.94±0.20°, preferably ±0.10°, and 28.44±0.20°, preferably ±0.10° in the powder X-ray diffraction.
(10) The crystal described in (9) above, wherein the crystal further has peaks at diffraction angles (2θ) of 17.48±0.20°, preferably ±0.10°, 20.90±0.20°, preferably ±0.10°, 21.66±0.20°, preferably ±0.10°, 35.50±0.20°, preferably ±0.10°, and 35.60±0.20°, preferably ±0.10° in the powder X-ray diffraction. the powder X-ray diffraction.
(11) A production method of a crystal of NeuAc alkali metal salt anhydrate, comprising adding or adding dropwise a solvent selected from the group consisting of alcohols and ketones to an aqueous N-acetylneuraminic acid solution containing an alkali metal-containing compound and having a pH of 3.0 to 9.0 to precipitate a crystal of NeuAc alkali metal salt anhydrate, and collecting the crystal of NeuAc alkali metal salt anhydrate from the aqueous solution.
(12) The production method described in (11) above, wherein the alkali metal salt is a sodium salt or a potassium salt.
(13) The production method described in (11) or (12) above, wherein the solvent selected from the group consisting of alcohols and ketones is a solvent selected from C1-C6 alcohols, acetone, methyl ethyl ketone, and diethyl ketone.

Advantage of the Invention

According to the present invention, a crystal of NeuAc alkali metal salt anhydrate, having high storage stability at normal temperature as well as in high temperature conditions, and a production process thereof are provided.

EMBODIMENTS FOR CARRYING OUT THE INVENTION

1. Crystal of NeuAc Alkali Metal Salt Anhydrate of the Present Invention

The crystal of NeuAc alkali metal salt anhydrate of the present invention is preferably a crystal of anhydrate of sodium salt or potassium salt of NeuAc.

Whether the crystal of NeuAc is a crystal of an anhydrate can be confirmed from the fact that the moisture content as measured using the Karl-Fisher method described later in Analysis Examples is 1.0 wt % or less, preferably 0.95 wt % or less, most preferably 0.9 wt % or less.

Whether the crystal of NeuAc anhydrate is a crystal of an alkali metal salt can be confirmed using an atomic absorption method or the ICP emission spectrometry described later in Analysis Examples.

As to the alkali metal confirmed by an atomic absorption method or the ICP emission spectrometry, the crystal can be confirmed to be a crystal of a monoalkali metal salt of NeuAc anhydrate by measuring the alkali metal content in the crystal.

For example, the crystal of NeuAc anhydrate can be confirmed to be a crystal of a monosodium salt by the fact that the sodium content in the crystal is 6.9±1.0 wt %, preferably 6.9±0.5 wt %, most preferably 6.9±0.3 wt %.

The crystal of NeuAc anhydrate can be confirmed to be a crystal of a monopotassium salt by the fact that the potassium content in the crystal is 11.3±1.0 wt %, preferably 11.3±0.5 wt %, most preferably 11.3±0.3 wt %.

Figure 1:
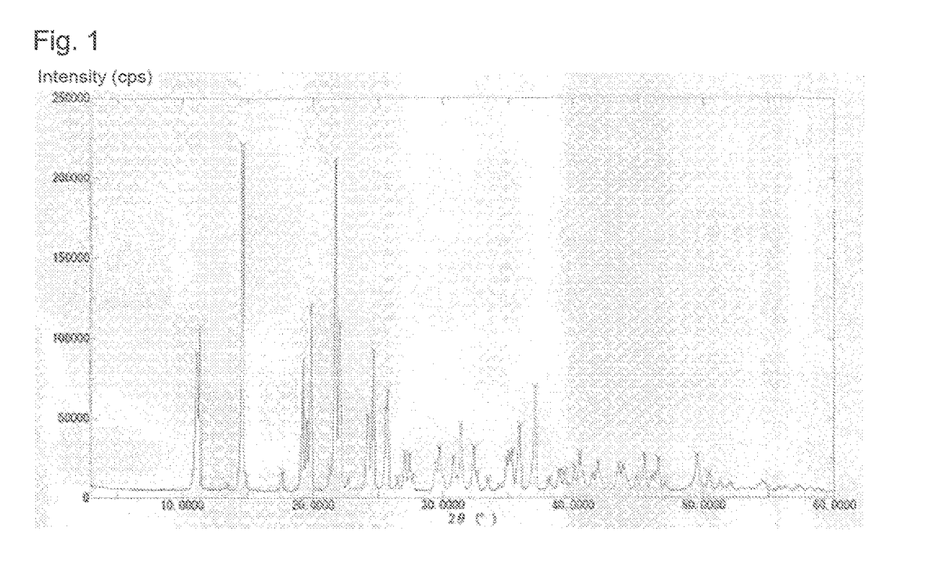
FIG. 1 Illustrating the results of powder X-ray diffraction of the crystal of NeuAc sodium salt anhydrate obtained in Example 1.
Figure 2:
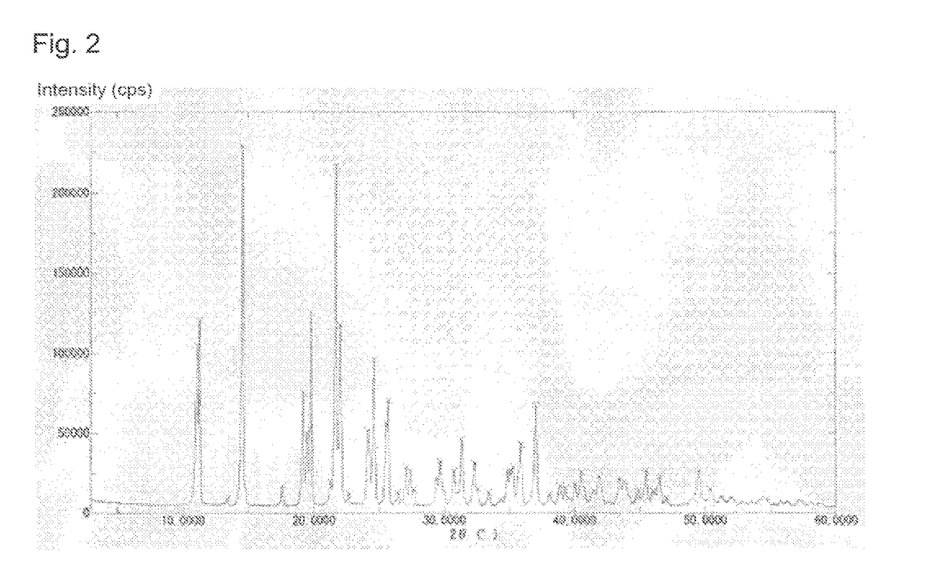
FIG. 2 Illustrating the results of powder X-ray diffraction of the crystal of NeuAc sodium salt anhydrate obtained in Example 2.
Figure 3:
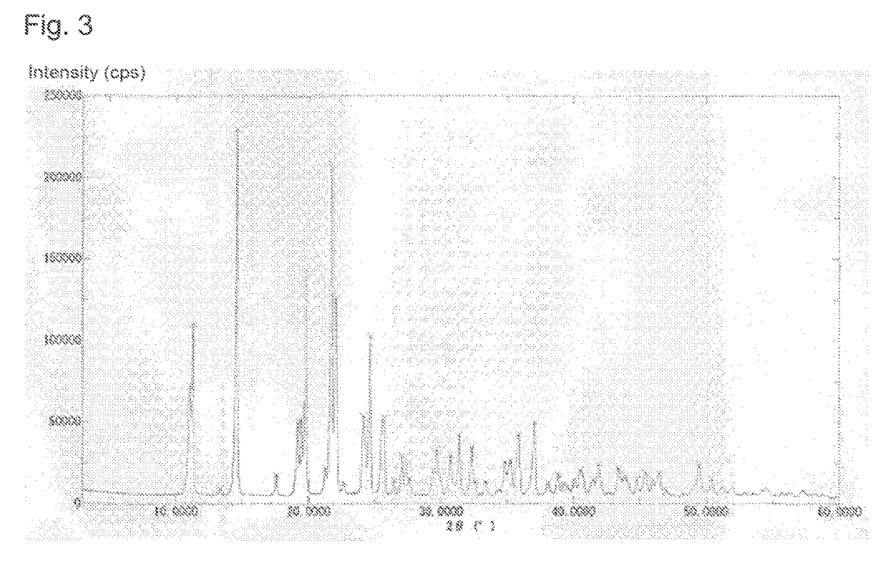
FIG. 3 Illustrating the results of powder X-ray diffraction of the crystal of NeuAc sodium salt anhydrate obtained in Example 3.

The crystal of the present invention includes a crystal of NeuAc sodium salt anhydrate, of which powder X-ray diffraction pattern using CuKa as the X-ray source is defined by the values shown in FIGS. 1 to 3 and Tables 1, 4 and 6. Here, FIGS. 1, 2 and 3 correspond to the analysis results of crystals of NeuAc sodium salt anhydrate of Tables 1, 4 and 6, respectively.

Figure 6:
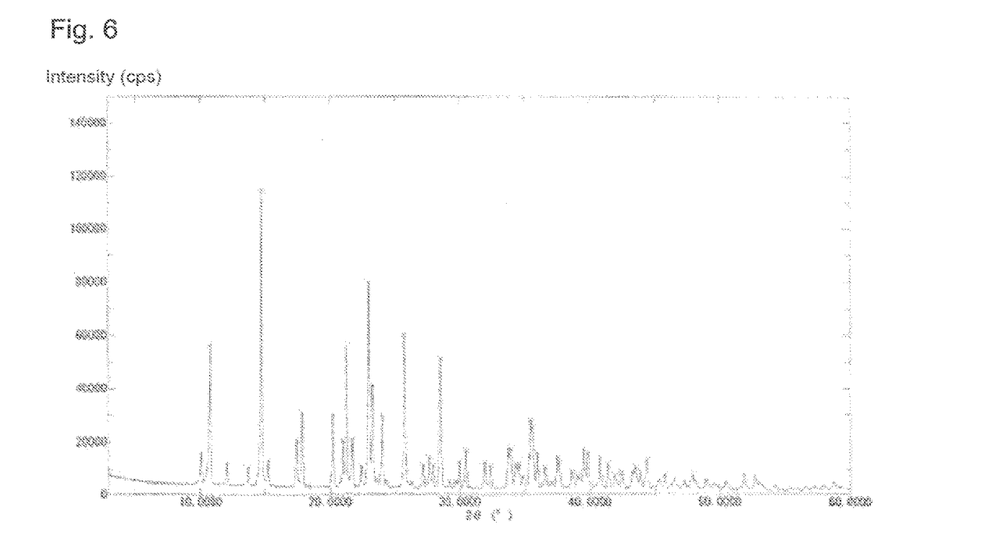
FIG. 6 Illustrating the results of powder X-ray diffraction of the crystal of NeuAc potassium anhydrate obtained in Example 4.
Figure 7:
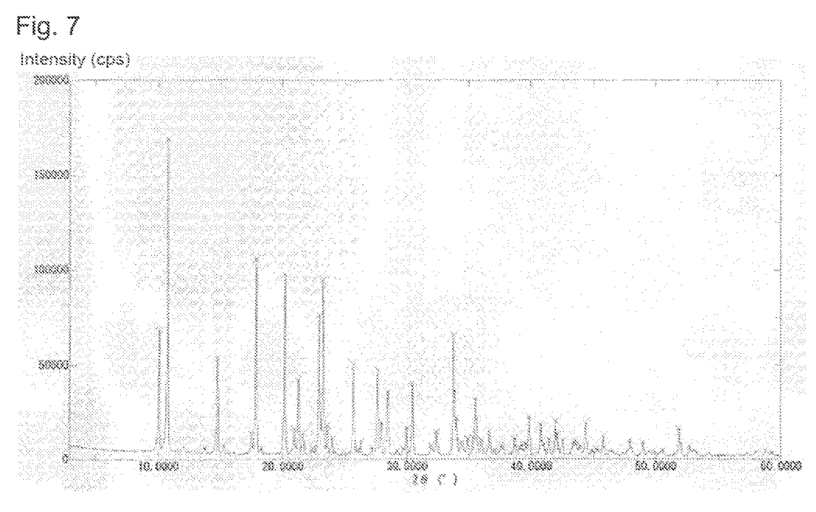
FIG. 7 Illustrating the results of powder X-ray diffraction of the crystal of NeuAc potassium anhydrate obtained in Example 5.
Figure 8:
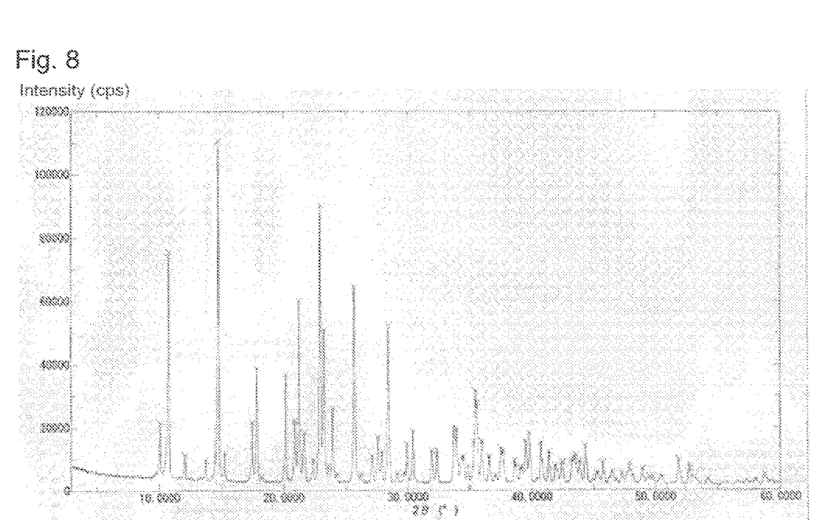
FIG. 8 Illustrating the results of powder X-ray diffraction of the crystal of NeuAc potassium anhydrate obtained in Example 6.

Also, the crystal of the present invention includes a crystal of NeuAc potassium salt anhydrate, of which powder X-ray diffraction pattern using CuKα as the X-ray source is defined by the values shown in FIGS. 6 to 8 and Tables 8, 11 and 13. Here, FIGS. 6, 7 and 8 correspond to the analysis results of crystals of NeuAc potassium salt anhydrate of Tables 8, 11 and 13, respectively.

Figure 4:
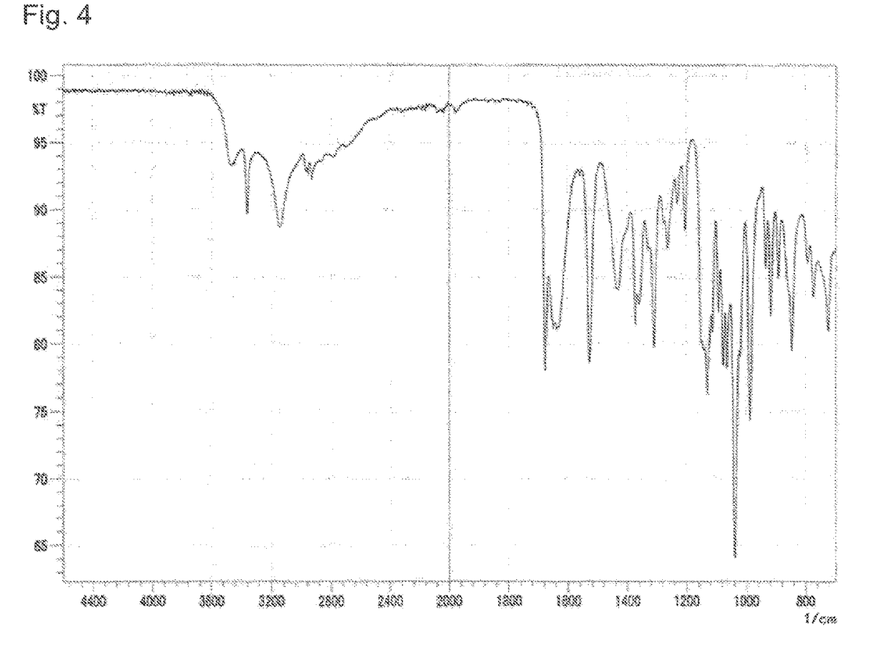
FIG. 4 Illustrating the results of infrared spectroscopic (IR) analysis of the crystal of NeuAc sodium salt anhydrate obtained in Example 2.

Further, the crystal of the present invention includes a crystal of NeuAc sodium salt anhydrate showing the infrared absorption spectrum illustrated in FIG. 4 when subjected to the infrared spectroscopic (IR) analysis described later in Analysis Examples.

Figure 9:
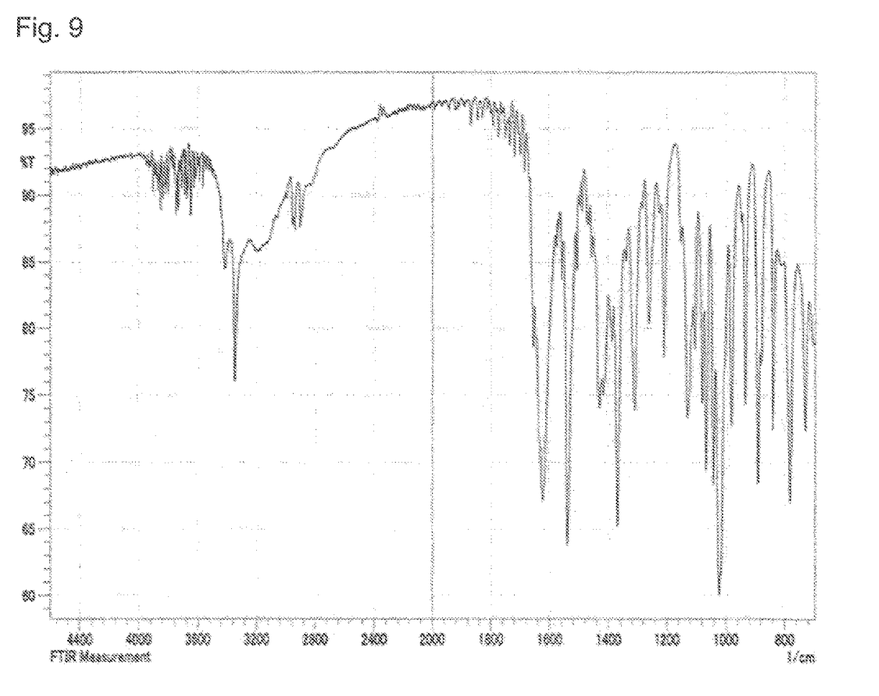
FIG. 9 Illustrating the results of infrared spectroscopic (IR) analysis of the crystal of NeuAc potassium anhydrate obtained in Example 4.

Also, a crystal showing the infrared absorption spectrum illustrated in FIG. 9 when subjected to IR analysis in the same manner as above can be recited as the crystal of NeuAc potassium salt anhydrate of the present invention.

2. Process for Producing Crystal of NeuAc Alkali Metal Salt Anhydrate of the Present Invention The process for producing the crystal of NeuAc alkali metal salt anhydrate of the present invention is a process comprising adding or adding dropwise a solvent selected from the group consisting of alcohols and ketones to an aqueous NeuAc solution containing an alkali metal-containing compound and having a pH of 3.0 to 9.0, preferably from 4.5 to 8.5, most preferably from 5.5 to 7.5, to precipitate a crystal of NeuAc alkali metal salt anhydrate, and collecting the crystal of NeuAc alkali metal salt anhydrate from the aqueous solution.

NeuAc contained in the aqueous NeuAc solution may be produced by any of a fermentation method, an enzyme method, an extraction method from natural products, a chemical synthesis method and other production methods.

In the case where a solid material that obstructs crystallization is contained in the aqueous NeuAc solution, the solid material can be removed using centrifugal separation, filtration, a ceramic filter, and the like. In the case where a water-soluble impurity or salt that obstructs crystallization is contained in the aqueous NeuAc solution, the water-soluble impurity or salt can be removed by passing the aqueous solution through a column packed with ion exchange resin, and the like.

The NeuAc concentration in the aqueous solution is 200 g/L or more, preferably 300 g/L or more, more preferably 400 g/L or more, still more preferably 500 g/L or more, most preferably 600 g/L or more. In order to adjust the concentration in the aqueous solution to the concentration above, the aqueous solution can be concentrated by a general concentration method such as heating concentration method or vacuum concentration method.

The alkali metal may be preferably sodium or potassium.

The alkali metal-containing compound includes a basic compound such as alkali metal hydroxide, alkali metal carbonate and alkali metal as a simple substance, and a neutral salt such as alkali metal sulfate, alkali metal nitrate and alkali metal chloride.

In the case where the alkali metal is sodium, the basic compound includes, for example, sodium hydroxide, sodium carbonate, and sodium as a simple substance, and the neutral salt includes, for example, sodium sulfate, sodium nitrate, and sodium chloride.

In the case where the alkali metal is potassium, the basic compound includes, for example, potassium hydroxide, potassium carbonate, and potassium as a simple substance, and the neutral salt includes, for example, potassium sulfate, potassium nitrate, and potassium chloride.

In the case of using a basic compound as the alkali metal-containing compound, an aqueous NeuAc solution containing an alkali metal-containing compound and having a pH of 3.0 to 9.0, preferably from 4.5 to 8.5, most preferably from 5.5 to 7.5, can be obtained by adjusting the pH of the aqueous NeuAc solution by use of the basic compound.

Alcohols may be C1-C6 alcohols, preferably C1-C3 alcohols, more preferably alcohols selected from the group consisting of methanol, ethanol, n-propanol and isopropyl alcohol, most preferably alcohols selected from the group consisting of methanol and ethanol.

Ketones may be ketones selected from acetone, methyl ethyl ketone and diethyl ketone, preferably acetone.

The temperature of the aqueous solution at the time of adding or adding dropwise a solvent selected from the group consisting of alcohols and ketones may be any temperature as long as NeuAc is not decomposed, but in order to decrease the degree of solubility and thereby enhance the crystallization rate of the crystal of NeuAc sodium salt anhydrate, the temperature may be 80° C. or less, preferably 70° C. or less, more preferably 60° C. or less, still more preferably 50° C. or less, most preferably 40° C. or less.

An amount of the solvent selected from the group consisting of alcohols and ketones to be added or added dropwise may be from 1 to 8 times, preferably from 2 to 6 times, most preferably from 3 to 5 times, in terms of the amount of the aqueous solution.

The time for which the solvent selected from alcohols and ketones is added or added dropwise may be from 1 to 48 hours, preferably from 3 to 30 hours, most preferably from 5 to 20 hours.

In the step of adding or adding dropwise the solvent selected from alcohols and ketones, before precipitation of a crystal of NeuAc alkali metal salt anhydrate, a crystal of NeuAc alkali metal salt anhydrate may be added as a seed crystal so that the concentration in the aqueous solution can be from 0.2 to 25 g/L, preferably from 0.5 to 10 g/L, most preferably from 2 to 5 g/L.

The time at which the seed crystal is added may be within 1 to 5 hours, preferably within 1 to 4 hours, most preferably within 1 to 3 hours, after adding dropwise or adding the solvent selected from alcohols and ketones is started.

After a crystal of NeuAc alkali metal salt anhydrate is precipitated as above, the precipitated crystal may be further matured for 1 to 48 hours, more preferably for 1 to 24 hours, most preferably for 1 to 12 hours.

The "matured" indicates to grow the crystal by once stopping the step of adding or adding dropwise the solvent selected from the group consisting of alcohols and ketones.

After the crystal is matured, the step of adding or adding dropwise the solvent selected from the group consisting of alcohols and ketones may be restarted.

The method for collecting the crystal of NeuAc alkali metal salt anhydrate is not particularly limited but may include pressure filtration, suction filtration, centrifugal separation, and the like. Furthermore, in order to reduce the adhesion of the mother liquid and thereby improve the quality of the crystal, the crystal may be appropriately washed. The solution used for crystal washing is not particularly limited, but water, methanol, ethanol, acetone, n-propanol, isopropyl alcohol, and a solution prepared by mixing in an arbitrary ratio one kind or a plural kinds of members selected from these may be used.

The thus-obtained wet crystal is dried, whereby a final product can be obtained. As for the drying conditions, any method may be used as long as the form of NeuAc alkali metal salt anhydrate can be maintained, and reduced-pressure drying, fluidized bed drying, forced air drying and the like may be applied. The drying temperature may be any temperature as long as the adhered water can be removed, but the temperature may be preferably 80° C. or less, more preferably 60° C. or less.

By employing the above-described crystallization conditions, a high-purity crystal of NeuAc alkali metal salt anhydrate can be obtained. The purity of the crystal of NeuAc alkali metal salt anhydrate may be 97% or more, preferably 98% or more, more preferably 99% or more, most preferably 99.5% or more.

The crystal of NeuAc alkali metal salt anhydrate, which can be produced by the production process above, includes, for example, a crystal of NeuAc sodium salt anhydrate, of which powder X-ray diffraction pattern using CuKa as the X-ray source is defined by the values shown in FIGS. 1 to 3 and Tables 1, 4 and 6, and a crystal of NeuAc potassium salt anhydrate, defined by the values shown in FIGS. 6 to 8 and Tables 8, 11 and 13.

ANALYSIS EXAMPLES (1) Powder X-Ray Diffraction

The measurement was performed using a powder X-ray diffraction apparatus (XRD), Ultima IV (manufactured by Rigaku Corporation), according to the instruction book.

(2) Measurement of Degree of Solubility

A crystal of NeuAc sodium salt anhydrate, a crystal of NeuAc potassium salt anhydrate, or a crystal of known NeuAc dihydrate was added to water adjusted to respective temperatures until each crystal was caused to remain undissolved and after keeping the solution for a sufficient time under stirring, the supernatant containing no crystal was collected and measured for the concentration by using the following HPLC analysis conditions.

Guard column: Shodex SUGAR SH-G ϕ6.0×50 mm

Column: SUGAR SH1011 ϕ8.0×300 mm×2 columns in series

Column temperature: 60° C.

Buffer: an aqueous 0.005 mol/L sulfuric acid solution

Flow velocity: 0.6 mL/min

Detector: UV detector (wavelength: 210 nm)

(3) Measurement of Moisture Content of Crystal by Karl-Fisher Method

The measurement was performed using MKA-510N/MKS-510N (manufactured by Kyoto Electronics Manufacturing Co., Ltd.) according to the instruction book.

(4) Measurement of Sodium or Potassium Content

The measurement was performed using an ICP emission spectrometry, Model ICPS-8100 (manufactured by Shimadzu Corporation), according to the instruction book.

(5) Measurement of Melting Point

The measurement was performed using Melting Point M-565 (manufactured by BUCHI) according to the instruction book.

(6) Infrared Spectroscopic (IR) Analysis

The measurement was performed using Model FTIR-8400 (manufactured by Shimadzu Corporation) according to the instruction book.

Reference Example 1

Acquisition of Noncrystalline Amorphous of NeuAc Sodium Salt:

A crystal of NeuAc anhydrate (1,472.3 g) was dissolved in water, and the pH was adjusted to 6.74 by using sodium hydroxide to make 4,400 mL of NeuAc sodium salt-containing aqueous solution. Part of this aqueous solution was freeze-dried to obtain a white powder. The powder X-ray diffraction of the powder was measured, as a result, an X-ray diffraction peak was not confirmed. The powder was therefore found to be a noncrystalline amorphous.

Reference Example 2

Acquisition of Noncrystalline Amorphous of NeuAc Potassium Salt:

A crystal of NeuAc dihydrate (89.6 g) was dissolved in water, and the pH was adjusted to 6.88 by using potassium hydroxide to make 800 mL of NeuAc potassium salt-containing aqueous solution. This aqueous solution was freeze-dried to obtain a white powder. The powder X-ray diffraction of the powder was measured, as a result, an X-ray diffi action peak was not confirmed The powder was therefore found to be a noncrystalline amorphous.

Examples are described below, but the present invention is not limited to the following Examples.

Example 1

Acquisition of Crystal of NeuAc Sodium Salt Anhydrate (1)

A crystal of NeuAc anhydrate (1,472.3 g) was dissolved in water, and the pH was adjusted to 6.74 by using sodium hydroxide to make 4,400 mL. This aqueous solution was concentrated to 2.0 L, and a 50 mL portion of the obtained concentrate was used for the next step.

While maintaining 50 mL of the concentrated solution at 40° C., 200 mL (4-fold amount) of methanol was added dropwise over 8 hours to precipitate a crystal. The crystal slurry was cooled to 10° C., and the crystal was then collected by filtration, washed with an aqueous 80% methanol solution and dried under reduced pressure at 25° C. to obtain 33.6 g of a crystal.

The results of powder X-ray diffraction of the crystal are shown in Table 1. In the Table, "2θ" indicates the diffraction angle (2θ), and "Relative Intensity" indicates the relative intensity ratio ($I/I_0$). The results when the relative intensity ratio was 5 or more are shown.

TABLE 1

| 2θ | Relative Intensity |
|---|---|
| 11.14 | 42 |
| 11.32 | 49 |
| 13.46 | 5 |
| 14.62 | 100 |
| 17.60 | 8 |
| 19.18 | 40 |
| 19.48 | 22 |
| 19.82 | 55 |
| 21.30 | 9 |
| 21.72 | 96 |
| 22.04 | 50 |
| 22.70 | 6 |
| 24.16 | 24 |
| 24.64 | 42 |
| 25.58 | 26 |
| 25.72 | 31 |
| 26.48 | 6 |
| 27.10 | 13 |
| 27.44 | 13 |
| 27.70 | 7 |
| 29.44 | 11 |
| 29.76 | 15 |
| 30.78 | 12 |
| 31.40 | 22 |
| 32.38 | 15 |
| 32.60 | 8 |
| 33.46 | 6 |
| 34.88 | 12 |
| 35.10 | 13 |
| 35.28 | 14 |
| 35.90 | 21 |
| 37.06 | 32 |
| 38.12 | 6 |
| 38.92 | 9 |
| 39.32 | 8 |
| 40.10 | 10 |
| 40.52 | 13 |
| 41.56 | 7 |
| 41.96 | 11 |
| 43.48 | 10 |
| 43.84 | 10 |
| 44.88 | 7 |
| 45.48 | 13 |
| 46.04 | 7 |
| 46.54 | 12 |
| 47.10 | 5 |
| 49.52 | 13 |
| 50.42 | 8 |

The sodium content of the crystal as measured by the ICP emission spectrometry was 7.1 wt % and substantially coincided with the theoretical value (6.9 wt %) of a monosodium salt. In addition, the amount of water contained in the crystal was 1.0 wt % or less.

From these results, the crystal was found to be a crystal of NeuAc sodium salt anhydrate.

Various physical properties of the crystal are shown in Table 2. As for the pH, an aqueous solution at 100 g/L in terms of NeuAc sodium salt was measured.

TABLE 2

| Water % | Sodium Content % | Melting Point ° C. | pH |
|---|---|---|---|
| 0.71 | 7.1 | 187.5 | 6.74 |

Figure 5:
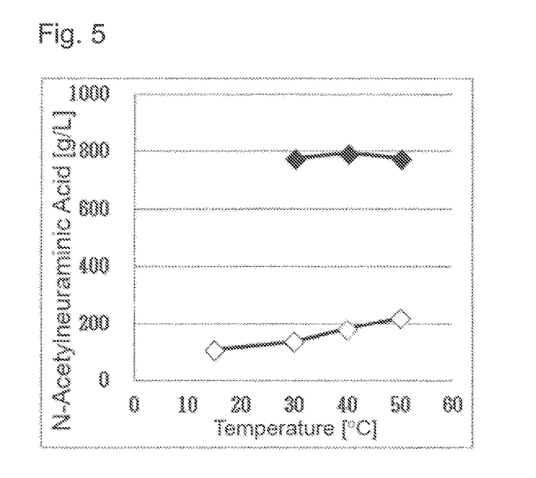
FIG. 5 Illustrating the degrees of solubility of the crystal of NeuAc sodium salt anhydrate obtained in Example 1 and a crystal of known NeuAc dihydrate; the vertical axis indicates the concentration (g/L) of NeuAc in terms of an anhydrate and the horizontal axis indicates the temperature (° C.).

The degrees of solubility in water of the crystal of NeuAc sodium salt anhydrate obtained above and a crystal of NeuAc dihydrate are illustrated in FIG. 5.

It was revealed that the crystal of NeuAc sodium salt anhydrate has a large degree of solubility compared with the degree of solubility of the crystal of known NeuAc dihydrate and has excellent solubility.

With respect to the crystal of NeuAc sodium salt anhydrate and the noncrystalline amorphous of NeuAc sodium salt acquired in Reference Example 1, the weight change under an atmosphere of 25° C. and humidity 66% was compared, and the results are shown in Table 3.

TABLE 3

| Elapsed Time [h] | 0 | 3 | 7 | 24 |
|---|---|---|---|---|
| Crystal of sodium salt | 0.00 | −0.04 | −0.02 | −0.04 |
| Noncrystalline amorphous | 0.00 | 9.47 | 12.2 | 15.9 |

(Rate of Weight Change [%])

The noncrystalline amorphous of NeuAc sodium salt exhibited a marked weight increase due to moisture absorption and deliquesced when 24 hours had passed. On the other hand, in the crystal of NeuAc sodium salt anhydrate, a weight increase was not recognized, and it was therefore revealed that moisture absorption can be suppressed by crystallization.

In addition, the melting point of the crystal of NeuAc sodium salt anhydrate is 187.5° C. and is higher than the melting point of around 100° C. of known NeuAc sodium salt trihydrate. It was therefore revealed that the crystal of NeuAc sodium salt anhydrate is stable even under high temperature conditions.

Example 2

Acquisition of Crystal of NeuAc Sodium Salt Anhydrate (2)

While maintaining 50 mL of the concentrated solution prepared in Example 1 at 25° C., 12.5 mL of ethanol was added dropwise over 2 hours. The crystal acquired in Example 1 was added as a seed crystal to precipitate a crystal. After maturing the crystal over 4 hours, the temperature was raised to 40° C., and 137.5 mL (final addition amount: 3-fold amount) of ethanol was added dropwise over 13 hours. The crystal slurry was cooled to 10° C. and matured for 3 hours, and the crystal was then collected by filtration, washed with an aqueous 80% ethanol solution and dried under reduced pressure at 25° C. to obtain 36.0 g of a crystal.

The results of powder X-ray diffraction of the crystal are shown in Table 4. In the Table, "2θ" indicates the diffraction angle (2θ), and "Relative Intensity" indicates the relative intensity ratio (I/I$_0$). The results when the relative intensity ratio was 5 or more are shown.

TABLE 4

| 2θ | Relative Intensity |
|---|---|
| 11.12 | 46 |
| 11.30 | 53 |
| 13.46 | 5 |
| 14.60 | 100 |
| 17.60 | 8 |
| 19.16 | 33 |
| 19.46 | 22 |
| 19.80 | 55 |
| 21.28 | 9 |
| 21.70 | 95 |
| 22.02 | 52 |
| 22.68 | 6 |
| 24.14 | 23 |
| 24.62 | 42 |
| 25.56 | 25 |
| 25.70 | 31 |

TABLE 4-continued

| 2θ | Relative Intensity |
|---|---|
| 26.44 | 6 |
| 27.08 | 13 |
| 27.42 | 12 |
| 27.66 | 7 |
| 29.44 | 10 |
| 29.72 | 15 |
| 30.76 | 12 |
| 31.36 | 21 |
| 32.34 | 14 |
| 32.58 | 7 |
| 33.42 | 6 |
| 34.82 | 12 |
| 35.06 | 12 |
| 35.26 | 13 |
| 35.86 | 19 |
| 37.04 | 30 |
| 38.10 | 6 |
| 38.90 | 8 |
| 39.30 | 8 |
| 40.08 | 8 |
| 40.50 | 12 |
| 41.50 | 7 |
| 41.90 | 11 |
| 43.46 | 10 |
| 43.80 | 9 |
| 44.86 | 7 |
| 45.46 | 12 |
| 46.00 | 7 |
| 46.52 | 11 |
| 47.08 | 5 |
| 49.50 | 12 |
| 50.40 | 7 |

The powder X-ray diffraction pattern and physical properties of the crystal were substantially the same as those of the crystal of NeuAc sodium salt anhydrate obtained in Example 1, and it was therefore understood that the crystal is also a crystal of NeuAc sodium salt anhydrate.

Various physical properties of the crystal are shown in Table 5. As for the pH, an aqueous solution at 100 g/L in terms of NeuAc sodium salt was measured.

TABLE 5

| Water % | Sodium Content % | Melting Point ° C. | pH |
|---|---|---|---|
| 0.82 | 7.1 | 188.1 | 6.8 |

Example 3

Acquisition of Crystal of NeuAc Sodium Salt Anhydrate (3)

While maintaining 50 mL of the concentrated solution prepared in Example 1 at 25° C., 200 mL (4-fold amount) of methanol was added dropwise over 8 hours to precipitate a crystal. The crystal slurry was cooled to 10° C., and the crystal was then collected by filtration, washed with an aqueous 80% methanol solution and dried under reduced pressure at 25° C. to obtain 32.7 g of a crystal.

The results of powder X-ray diffraction of the crystal are shown in Table 6. In the Table, "2θ" indicates the diffraction angle (2θ), and "Relative Intensity" indicates the relative intensity ratio (I/I$_0$). The results when the relative intensity ratio was 5 or more are shown.

TABLE 6

| 2θ | Relative Intensity |
|---|---|
| 11.02 | 32 |
| 11.28 | 49 |
| 13.44 | 5 |
| 14.58 | 100 |
| 17.58 | 8 |
| 19.16 | 22 |
| 19.42 | 23 |
| 19.76 | 63 |
| 21.24 | 10 |
| 21.68 | 92 |
| 22.00 | 55 |
| 22.66 | 6 |
| 24.12 | 24 |
| 24.60 | 45 |
| 25.54 | 23 |
| 25.68 | 23 |
| 26.44 | 7 |
| 27.06 | 13 |
| 27.40 | 11 |
| 27.66 | 7 |
| 29.42 | 9 |
| 29.68 | 15 |
| 30.72 | 13 |
| 31.34 | 19 |
| 32.30 | 16 |
| 32.58 | 7 |
| 33.38 | 7 |
| 34.80 | 12 |
| 35.28 | 12 |
| 35.84 | 19 |
| 37.02 | 22 |
| 38.08 | 6 |
| 38.82 | 8 |
| 39.32 | 6 |
| 39.62 | 5 |
| 40.06 | 7 |
| 40.58 | 10 |
| 41.50 | 7 |
| 41.92 | 11 |
| 43.40 | 10 |
| 43.86 | 8 |
| 44.80 | 7 |
| 45.42 | 9 |
| 46.00 | 7 |
| 46.50 | 9 |
| 49.50 | 11 |
| 50.42 | 7 |

The powder X-ray diffraction pattern of the crystal was substantially the same as those of the crystals of NeuAc sodium salt anhydrate obtained in Examples 1 and 2, and it was therefore understood that the crystal is also a crystal of NeuAc sodium salt anhydrate.

With respect to the crystal of NeuAc sodium salt anhydrate and a crystal of known NeuAc dihydrate, the degree of coloration when stored in a closed system at 60° C. was compared, and the results are shown in Table 7. The degree of coloration is expressed by transmittance T % 430 nm=100×10$^{-A}$ (A=Abs: 430 nm, 1 cm).

TABLE 7

| Elapsed Time [days] | 0 | 3 | 6 |
|---|---|---|---|
| Crystal of sodium salt | 99.98 | 100.0 | 100.0 |
| Crystal of dihydrate | 100.1 | 73.26 | 50.46 |

(Transmittance T % 430 nm)

It was found that the coloration of the crystal of NeuAc sodium salt anhydrate during storage is extremely low compared with the crystal of known NeuAc dihydrate.

Example 4

Acquisition of Crystal of NeuAc Potassium Salt Anhydrate (1)

A crystal of NeuAc dihydrate (1,451 g) was dissolved in water, and the pH was adjusted to 6.87 by using potassium hydroxide to make 2.9 L. This aqueous solution was concentrated to 1.9 L, and a 250 mL portion of the obtained concentrate was used for the next step.

While maintaining 250 mL of the concentrated solution at 20° C., 750 mL (3-fold amount) of methanol was added dropwise over 1 hour to precipitate a crystal. The crystal was collected by filtration, washed with an aqueous 75% methanol solution and then dried under reduced pressure at 25° C. to obtain 144.7 g of a crystal.

The results of powder X-ray diffraction of the crystal are shown in Table 8. In the Table, "2θ" indicates the diffraction angle (2θ), and "Relative Intensity" indicates the relative intensity ratio ($I/I_0$). The results when the relative intensity ratio was 5 or more are shown.

TABLE 8

| 2θ | Relative Intensity |
|---|---|
| 10.08 | 15 |
| 10.76 | 50 |
| 12.08 | 11 |
| 13.78 | 10 |
| 14.78 | 100 |
| 15.26 | 12 |
| 17.48 | 18 |
| 17.88 | 27 |
| 20.18 | 27 |
| 20.92 | 18 |
| 21.26 | 50 |
| 21.68 | 19 |
| 22.34 | 10 |
| 22.94 | 70 |
| 23.20 | 36 |
| 23.54 | 6 |
| 23.94 | 27 |
| 24.26 | 5 |
| 25.66 | 53 |
| 26.24 | 5 |
| 27.12 | 11 |
| 27.66 | 13 |
| 27.90 | 10 |
| 28.46 | 45 |
| 29.18 | 5 |
| 29.72 | 5 |
| 29.96 | 12 |
| 30.44 | 15 |
| 31.94 | 11 |
| 32.38 | 10 |
| 33.74 | 16 |
| 33.96 | 16 |
| 34.36 | 10 |
| 34.56 | 11 |
| 34.88 | 7 |
| 35.34 | 14 |
| 35.50 | 25 |
| 35.64 | 23 |
| 35.98 | 14 |
| 36.06 | 9 |
| 36.60 | 10 |
| 37.12 | 5 |
| 37.56 | 13 |
| 37.66 | 11 |
| 38.62 | 8 |
| 38.74 | 7 |
| 39.08 | 7 |
| 39.20 | 6 |
| 39.54 | 16 |
| 39.84 | 15 |
| 40.76 | 13 |
| 41.42 | 11 |

TABLE 8-continued

| 2θ | Relative Intensity |
|---|---|
| 41.90 | 7 |
| 42.44 | 8 |
| 43.52 | 10 |
| 44.34 | 12 |
| 45.72 | 7 |
| 47.94 | 7 |

The potassium content of the crystal as measured by the ICP emission spectrometry was 11.5 wt % and substantially coincided with the theoretical value (11.3 wt %) of a monopotassium salt. In addition, the amount of water contained in the crystal was 1.0 wt % or less.

From these results, the crystal was found to be a crystal of NeuAc potassium salt anhydrate.

Various physical properties of the crystal are shown in Table 9. As for the pH, an aqueous solution at 100 g/L in terms of NeuAc potassium salt was measured.

TABLE 9

| Water % | Potassium Content % | Melting Point ° C. | pH |
|---|---|---|---|
| 0.58 | 11.5 | 174.6 | 6.6 |

Figure 10:
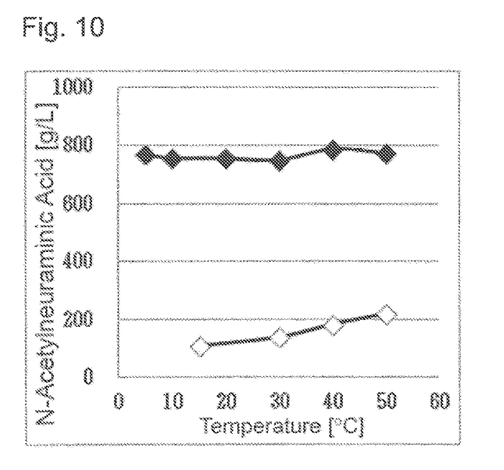
FIG. 10 Illustrating the degrees of solubility of the crystal of NeuAc potassium anhydrate obtained in Example 4 and a crystal of known NeuAc dihydrate; the vertical axis indicates the concentration (g/L) of NeuAc in terms of an anhydrate and the horizontal axis indicates the temperature (° C.).

The degrees of solubility in water of the crystal of NeuAc potassium salt anhydrate obtained above and a crystal of NeuAc dihydrate are illustrated in FIG. 10.

It was revealed that the crystal of NeuAc potassium salt anhydrate has a large degree of solubility compared with the degree of solubility of the crystal of known NeuAc dihydrate and has excellent solubility.

With respect to the crystal of NeuAc potassium salt anhydrate and the noncrystalline amorphous of NeuAc potassium salt acquired in Reference Example 2, the weight change under an atmosphere of 25° C. and humidity 66% was compared, and the results are shown in Table 10.

TABLE 10

| Elapsed Time [h] | 0 | 3 | 7 | 24 |
|---|---|---|---|---|
| Crystal of potassium salt | 0.00 | 0.06 | 0.00 | −0.06 |
| Noncrystalline amorphous | 0.00 | 1.49 | 4.36 | 7.71 |

(Rate of Weight Change [%])

The noncrystalline amorphous of NeuAc potassium salt exhibited a marked weight increase due to moisture absorption and deliquesced when 24 hours had passed. On the other hand, in the crystal of NeuAc potassium salt anhydrate, a weight increase was not recognized and it was therefore revealed that moisture absorption can be suppressed by crystallization.

In addition, the melting point of the crystal of NeuAc potassium salt anhydrate is 174.6° C. and is higher than the melting point of around 100° C. of known NeuAc sodium salt trihydrate. It was therefore revealed that the crystal of NeuAc potassium salt anhydrate is stable even under high temperature conditions.

Example 5

Acquisition of Crystal of NeuAc Potassium Salt Anhydrate (2)

A crystal of NeuAc dihydrate (1,145 g) was dissolved in water, and the pH was adjusted to 6.95 by using potassium hydroxide. The solution was concentrated to 1.5 L, 20 mL of water was added to 40 mL of the obtained concentrated solution, and then a 50 mL portion of the thus-obtained solution was used for the next step.

While maintaining 50 mL of the solution at 40° C., 60 mL of ethanol was added dropwise over 2 hours. The crystal acquired in Example 4 was added as a seed crystal to precipitate a crystal. After maturing the crystal over 6 hours, 140 mL (final addition amount: 4-fold amount) of ethanol was further added dropwise over 12 hours. The crystal slurry was cooled to 10° C. and matured for 3 hours, and the crystal was then collected by filtration, washed with an aqueous 80% ethanol solution and dried under reduced pressure at 25° C. to obtain 25.9 g of a crystal.

The results of powder X-ray diffraction of the crystal are shown in Table 11. In the Table, "2θ" indicates the diffraction angle (2θ), and "Relative Intensity" indicates the relative intensity ratio ($I/I_0$). The results when the relative intensity ratio was 5 or more are shown.

TABLE 11

| 2θ | Relative Intensity |
|---|---|
| 10.06 | 41 |
| 10.76 | 100 |
| 12.06 | 5 |
| 14.76 | 32 |
| 15.24 | 5 |
| 17.46 | 9 |
| 17.86 | 63 |
| 20.18 | 58 |
| 20.90 | 10 |
| 21.24 | 26 |
| 21.56 | 9 |
| 22.92 | 46 |
| 23.20 | 57 |
| 23.54 | 11 |
| 23.94 | 7 |
| 25.64 | 31 |
| 26.22 | 7 |
| 27.12 | 5 |
| 27.60 | 29 |
| 27.88 | 12 |
| 28.42 | 22 |
| 29.94 | 10 |
| 30.44 | 24 |
| 31.94 | 5 |
| 32.38 | 9 |
| 33.74 | 40 |
| 33.84 | 22 |
| 33.96 | 14 |
| 34.40 | 6 |
| 34.86 | 7 |
| 35.34 | 8 |
| 35.50 | 20 |
| 35.60 | 13 |
| 35.98 | 7 |
| 36.58 | 10 |
| 37.54 | 5 |
| 38.62 | 7 |
| 39.22 | 5 |
| 39.52 | 6 |
| 39.82 | 14 |
| 40.76 | 12 |
| 41.90 | 13 |
| 41.40 | 7 |
| 42.02 | 9 |
| 42.50 | 7 |
| 43.38 | 6 |
| 43.50 | 7 |
| 43.88 | 5 |
| 44.32 | 12 |
| 45.72 | 8 |
| 47.94 | 7 |
| 48.96 | 6 |

The powder X-ray diffraction pattern and physical properties of the crystal were substantially the same as those of the crystal of NeuAc potassium salt anhydrate obtained in Example 4, and it was therefore understood that the crystal is also a crystal of NeuAc potassium salt anhydrate.

Various physical properties of the crystal are shown in Table 12. As for the pH, an aqueous solution at 100 g/L in terms of NeuAc potassium salt was measured.

TABLE 12

| Water % | Potassium content % | Melting Point °C. | pH |
|---|---|---|---|
| 0.85 | 11.3 | 184.1 | 6.5 |

Example 6

Acquisition of Crystal of NeuAc Potassium Salt Anhydrate (3)

While maintaining 50 mL of the concentrated solution prepared in Example 5 at 50° C., 150 mL of methanol was added dropwise over 1 hour. The crystal acquired in Example 4 was added as a seed crystal to precipitate a crystal. After maturing the crystal over 1 hour, 50 mL (final addition amount: 4-fold amount) of methanol was further added dropwise over 10 hours. The crystal slurry was cooled to 10° C. and matured for 3 hours, and the crystal was then collected by filtration, washed with an aqueous 80% methanol solution and dried under reduced pressure at 25° C. to obtain 34.3 g of a crystal.

The results of powder X-ray diffraction of the crystal are shown in Table 13. In the Table, "2θ" indicates the diffraction angle (2θ), and "Relative Intensity" indicates the relative intensity ratio ($I/I_0$). The results when the relative intensity ratio was 5 or more are shown.

TABLE 13

| 2θ | Relative Intensity |
|---|---|
| 10.06 | 20 |
| 10.76 | 69 |
| 12.06 | 11 |
| 13.76 | 9 |
| 14.76 | 100 |
| 15.26 | 11 |
| 17.48 | 20 |
| 17.86 | 36 |
| 18.24 | 5 |
| 20.18 | 34 |
| 20.90 | 21 |
| 21.24 | 55 |
| 21.66 | 17 |
| 22.34 | 9 |
| 22.92 | 82 |
| 23.20 | 47 |
| 23.54 | 8 |
| 23.92 | 24 |
| 24.22 | 5 |
| 25.64 | 59 |
| 26.22 | 5 |
| 27.10 | 10 |
| 27.58 | 16 |
| 27.88 | 12 |
| 28.44 | 48 |
| 29.18 | 5 |
| 29.70 | 5 |
| 29.96 | 14 |
| 30.44 | 18 |
| 31.94 | 12 |

TABLE 13-continued

| 2θ | Relative Intensity |
|---|---|
| 32.36 | 12 |
| 33.72 | 18 |
| 33.96 | 18 |
| 34.38 | 10 |
| 34.52 | 10 |
| 34.88 | 8 |
| 35.34 | 15 |
| 35.50 | 29 |
| 35.60 | 26 |
| 35.96 | 15 |
| 36.58 | 10 |
| 37.12 | 5 |
| 37.52 | 13 |
| 37.62 | 12 |
| 38.62 | 9 |
| 38.72 | 8 |
| 39.06 | 7 |
| 39.18 | 7 |
| 39.50 | 15 |
| 39.80 | 17 |
| 40.76 | 14 |
| 41.40 | 12 |
| 41.88 | 8 |
| 42.46 | 9 |
| 43.24 | 9 |
| 43.34 | 10 |
| 43.50 | 11 |
| 43.82 | 9 |
| 44.30 | 13 |
| 45.22 | 6 |
| 45.70 | 9 |
| 46.48 | 6 |
| 47.26 | 6 |
| 47.92 | 9 |
| 48.96 | 7 |
| 49.52 | 5 |
| 49.80 | 5 |

The powder X-ray diffraction pattern of the crystal was substantially the same as those of the crystals of NeuAc potassium salt anhydrate obtained in Examples 4 and 5, and it was therefore understood that the crystal is also a crystal of NeuAc potassium salt anhydrate.

With respect to the crystal of NeuAc potassium salt anhydrate and a crystal of known NeuAc dihydrate, the degree of coloration when stored in a closed system at 60° C. was compared, and the results are shown in Table 14. The degree of coloration is expressed by transmittance T % 430 nm=$100 \times 10^{-A}$ (A=Abs: 430 nm, 1 cm).

TABLE 14

| Elapsed Time [days] | 0 | 3 | 6 |
|---|---|---|---|
| Crystal of potassium salt | 99.90 | 99.73 | 99.63 |
| Crystal of dihydrate | 100.1 | 73.26 | 50.46 |

(Transmittance T % 430 nm)

It was found that the coloration of the crystal of NeuAc potassium salt anhydrate during storage is extremely low compared with the crystal of known NeuAc dihydrate.

INDUSTRIAL APPLICABILITY

According to the present invention, a crystal of NeuAc alkali metal salt anhydrate, which is useful, for example, as a product, a raw material or an intermediate of health food, pharmaceuticals, cosmetics and the like, and a production process thereof are provided.

DESCRIPTION OF REFERENCE NUMERALS AND SIGNS

In FIG. 5, the black diamond indicates the crystal of NeuAc sodium salt anhydrate, and the white diamond indicates the crystal of NeuAc dihydrate.

In FIG. 10, the black diamond indicates the crystal of NeuAc potassium salt anhydrate, and the white diamond indicates the crystal of NeuAc dihydrate.

The invention claimed is:

1. A crystal of an alkali metal N-acetylneuraminate anhydrate.

2. The crystal according to claim 1, wherein the alkali metal N-acetylneuraminate anhydrate is a sodium salt or a potassium salt.

3. The crystal according to claim 1, wherein the alkali metal N-acetylneuraminate anhydrate is a sodium salt.

4. The crystal according to claim 1, wherein the alkali metal N-acetylneuraminate anhydrate is a potassium salt.

5. The crystal according to claim 3, wherein the crystal has peaks at diffraction angles (2θ) of 11.30±0.20°, 14.60±0.20°, 19.80±0.20°, 21.70±0.20°, and 22.02±0.20° in powder X-ray diffraction.

6. The crystal according to claim 5, wherein the crystal further has peaks at diffraction angles (2θ) of 11.12±0.20°, 19.16±0.20°, 24.62±0.20°, 25.70±0.20°, and 37.04±0.20° in powder X-ray diffraction.

7. The crystal according to claim 6, wherein the crystal further has peaks at diffraction angles (2θ) of 19.46±0.20°, 24.14±0.20°, 25.56±0.20°, 31.34±0.20°, and 35.86±0.20 in powder X-ray diffraction.

8. The crystal according to claim 4, wherein the crystal has peaks at diffraction angles (2θ) of 10.76±0.20°, 14.76±0.20°, 21.24±0.20°, 22.92±0.20°, and 25.64±0.20° in the powder X-ray diffraction.

9. The crystal according to claim 8, wherein the crystal further has peaks at diffraction angles (2θ) of 17.86±0.20°, 20.18±0.20°, 23.20±0.20°, 23.94±0.20°, and 28.44±0.20° in the powder X-ray diffraction.

10. The crystal according to claim 9, wherein the crystal further has peaks at diffraction angles (2θ ) of 17.48±0.20°, 20.90±0.20°, 21.66±0.20°, 35.50±0.20°, and 35.60±0.20° in the powder X-ray diffraction.

11. A process for producing a crystal of an alkali metal N-acetylneuraminate anhydrate, comprising adding or adding dropwise a solvent selected from the group consisting of alcohols and ketones to an aqueous N-acetylneuraminic acid solution containing an alkali metal-containing compound and having a pH of 3.0 to 9.0 to precipitate a crystal of an alkali metal N-acetylneuraminate anhydrate, and collecting the crystal of an alkali metal N-acetylneuraminate anhydrate from the aqueous solution.

12. The production process according to claim 11, wherein the alkali metal N-acetylneuraminate anhydrate is a sodium salt or a potassium salt.

13. The production process according to claim 12, wherein the solvent selected from the group consisting of alcohols and ketones is a solvent selected from C1-C6 alcohols, acetone, methyl ethyl ketone, and diethyl ketone.

14. The production process according to claim 11, wherein the solvent selected from the group consisting of alcohols and ketones is a solvent selected from C1-C6alcohols, acetone, methyl ethyl ketone, and diethyl ketone.

* * * * *